United States Patent [19]
Yaegaki

[11] Patent Number: 5,866,116
[45] Date of Patent: Feb. 2, 1999

[54] METHOD FOR REDUCING ORAL MALODOR

[76] Inventor: Ken Yaegaki, 9336—155A Street, Surrey, British Columbia, V3R 9B7, Canada

[21] Appl. No.: 788,304

[22] Filed: Jan. 24, 1997

[51] Int. Cl.$^6$ ...................................................... C12N 1/18
[52] U.S. Cl. ........................................................... 424/93.51
[58] Field of Search ............................................. 424/93.51

[56] References Cited

FOREIGN PATENT DOCUMENTS

| | | |
|---|---|---|
| 02124054 | 5/1990 | Japan . |
| 07258049 | 10/1995 | Japan . |
| WO 92/04037 | 3/1992 | WIPO . |

*Primary Examiner*—Jean C. Witz
*Attorney, Agent, or Firm*—Paul A. Guss; Mark M. Yang

[57] ABSTRACT

Yeast for making wine and beer, is placed on the subject's tongue to reduce oral malodor. About 30 to 100 milligrams of powdered yeast placed on the dorsal part of the subject's tongue just before he or she turns in for the evening, is optimal. Other methods of delivery yeast to the tongue include creams, solutions and Pills.

9 Claims, 2 Drawing Sheets

METHOD FOR REDUCING ORAL MALODOR

FIELD OF INVENTION

This invention relates to a method and product for reducing oral malodour.

BACKGROUND OF INVENTION

Halitosis, or oral malodour, is thought to be created by degraded epithelial cells of the tongue and the surface of the oral mucosa. Volatile sulphur compounds (such as hydrogen sulphide, methyl mercaptan, dimethyl sulphide) are produced by the putrefactive activities of bacteria in the saliva, the gingival crevice, the tongue coating and other places in the oral cavity. Tongue coating includes desquamated epithelial cells released from the oral mucosa, leukocytes from periodontal pockets, and bacteria. Leukocytes possess large quantities of sulphur-containing amino acids from which volatile sulphur compounds are made.

There have been many commercial attempts to reduce or mask oral malodour, including mouthwash and chewing gum. Their effects last perhaps a few hours.

The simplest method of removing the volatile sulphur compounds is to scrape the tongue (by brush or tongue scraper, for example). But this method has disadvantages. For example, scraping damages the oral mucosa (because the cells are strongly attached to the oral mucosa) and also produces a gag reflex if the dorsal portion of the tongue is touched.

PCT application #US91/06011 (Chaykin) discloses a method for reducing the undesirable side effects of eating vegetables like onions, garlic and beans; namely, ingesting active dry yeast in a form which retains substantial enzymatic activity under digestive conditions in the stomach and intestinal tract.

It is known informally that *Bacillus Natto* has been placed on the tongue during the day but that it had no or little effect on oral malodour.

SUMMARY OF INVENTION

According to this invention, an efficacious method for reducing oral malodour has been found. Microorganisms (as herein described, including powdered yeast) are placed on the subject's tongue and not swallowed, wherein said microorganisms are activated in the moist oral cavity of the subject and, when activated, have substantial enzymatic activity sufficient to render volatile sulphur compounds in the oral cavity into less smelly chemicals.

According to this invention, the yeast can be delivered to the subject's tongue in other ways, including cream, pill, chewing gum, solution and the like.

BRIEF DESCRIPTION OF DRAWINGS

Advantages of the present invention will become apparent from the following detailed description of the preferred embodiments. Experimental results are shown in the accompanying drawings, in which.

DETAILED DESCRIPTION OF THE PREFERRED EMBODIMENTS

It has been found that certain yeasts placed on a subject's tongue under certain conditions are effective to reduce oral malodour.

A dose of between 30 and 100 milligrams of yeast of the strain *Saccharomyces cerevisiae* in powdered form is sprinkled on the subject's tongue at the dorsal portion thereof. To maximize the opportunity of the yeast to be activated by the conditions of the oral cavity, the subject refrains from swallowing (both the yeast and saliva) to the extent possible (perhaps in the order of one to two minutes) and thereafter, refrains from ingesting drink or food. This process is naturally and best performed in the evening, just before the subject goes to bed.

Figure 1:
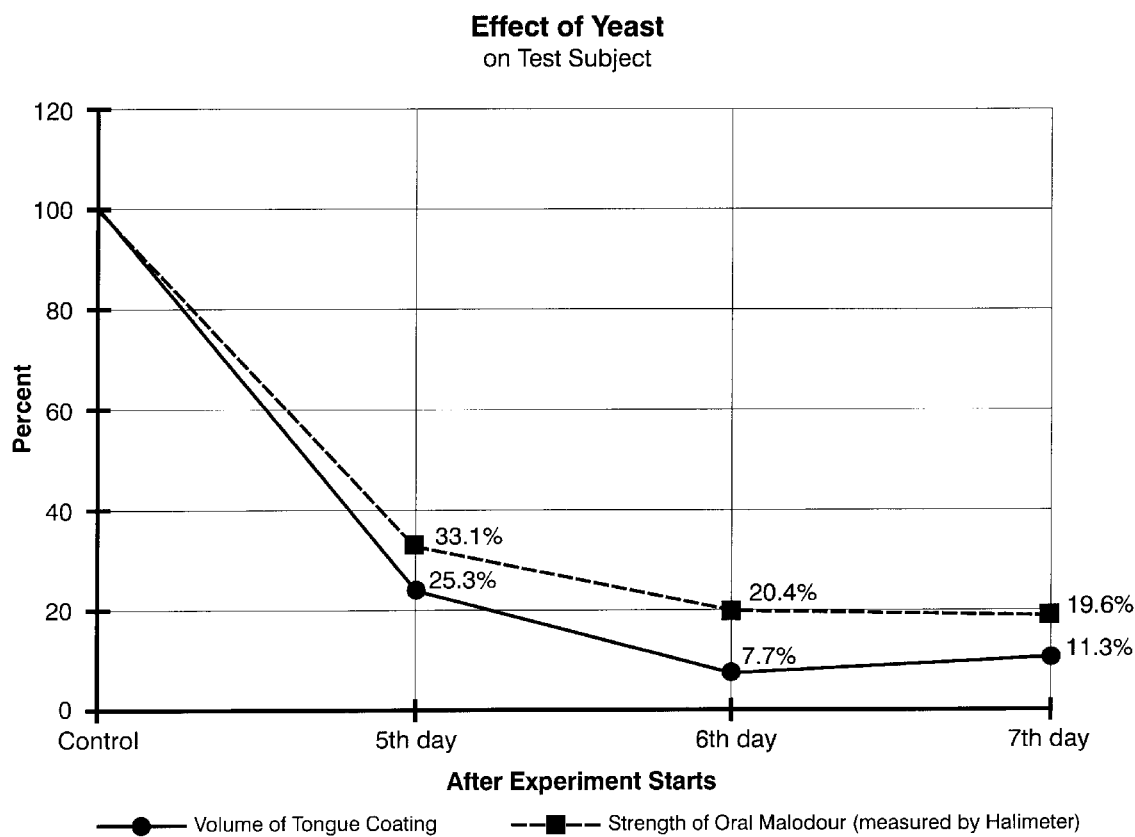
FIG. 1 is a graph which shows the effect of the method of the present invention over seven days.
Figure 2:
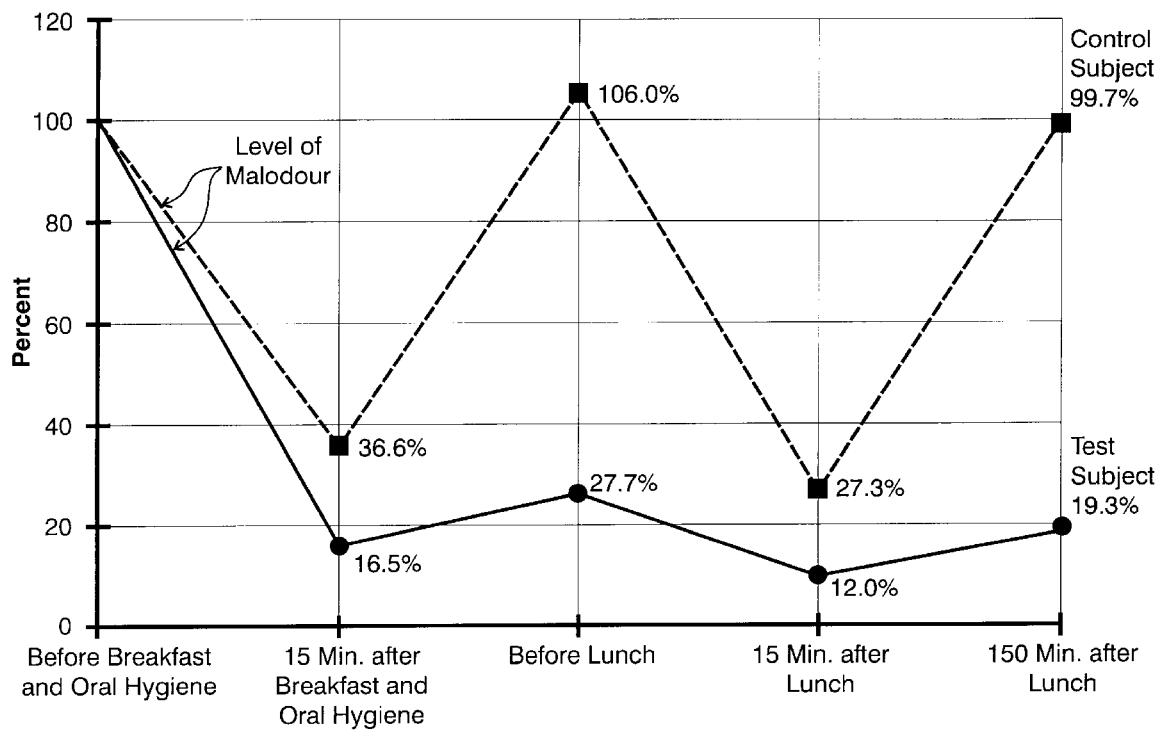
FIG. 2 is a graph which shows the effect of the method of the present invention relative to a control subject during a portion of the seventh day.

FIGS. 1 and 2 show the results of an experiment conducted over seven days using every evening 50 milligrams of *Saccharomyces cerevisiae* ("All Purpose Wine Yeast", sold by Lallemand Inc. of Montreal, Canada). They show a reduction of malodour and tongue coating towards levels of 20% and 10% of the original conditions. Malodour was measured conventionally in units of "parts per billion" with a Halimeter device (manufactured by Interscan Co. of Chatsworth, Calif., USA). Tongue coating was measured conventionally in units of milligrams, by excluding moisture and saliva from the tongue by surrounding the tongue with cotton balls; removing saliva on the dorsal portion of the tongue by a stream of air and pure pulp tissue paper; and removing the tongue coating from the terminal sulcus to the apex of the tongue with a tongue scraper of the spoon type.

Dosages outside the 30 to 100 milligrams range are possible. Increased dosage increases effectiveness but may increase an undesirable aftertaste in the subject's mouth.

Delivery methods of the yeast other than sprinkling the powdered form on the subject's tongue, as described above, can be employed.

Powdered yeast can be conventionally delivered in a gelatin capsule or can be conventionally compacted into the form of gum, candy, tablet, lozenge, or pill with starch, methylcellulose or other common chemical binders that do not activate or destroy the yeast. The capsule or other compact form is placed on the tongue and naturally dissolved in the mouth to release and activate the yeast.

Alternatively, a solution can be made by the subject from, for example, about 500 milligrams of powdered yeast mixed in about 20 millilitres of water. Then the subject gargles and rinses with the solution, after which approximately the equivalent of 50 milligrams of powdered yeast (or approximately ten percent of the initial powdered yeast) will be left on the tongue. The gargling should deposit the yeast mostly on the dorsal portion of the subject's tongue.

Alternatively, a cream can be made conventionally formed of yeast with glycerine or similar chemicals that do not activate or destroy yeast, and not with any elements, like water, that will activate the yeast. The cream can be applied to the dorsal portion of the tongue.

Alternatively, a toothpaste can be conventionally formed of yeast with glycerine or similar chemicals that do not activate or destroy yeast, and not with any elements, like water, that will activate the yeast. The cream can be applied to the dorsal portion of the tongue.

Alternatively, yeast is commercially available in liquid form and the appropriate concentration and quantity can be rinsed, gargled and evacuated, so that the equivalent of about 30 to 100 milligrams of yeast in powdered form is left on the tongue.

The effectiveness of the method when employed during the day, is good but not as good (in terms of duration and effect) as when employed just before the subject goes to bed for the evening. It is believed that tongue coating is formed mainly while sleeping.

For the purposes of this invention and this application for patent, the term "microorganism" includes, in particular, yeasts of the strain Saccharomyces which are commonly used to ferment fruits to make wine and beer; and includes, generally, any other microorganism which has substantial enzymatic activity for a long period of time in the conditions of the oral cavity of a subject (typically involving pH, temperature, quantity of volatile sulphur compounds and the like). The microorganism (or product containing the microorganism) may be viable or, if not viable, contain enzymes in active form. The microorganism may be in liquid or powdered form. To be substantially active enzymatically, means to be substantially effective to render volatile sulphur compounds in the oral cavity into less smelly chemicals.

While the principles of the invention have now been made clear, there will be immediately obvious to those skilled in the art, many modifications of arrangements, proportions, and components used in the practice of the invention, and otherwise, which are particularly adapted for specific environments and operational requirements without departing from those principles. The claims are therefore intended to cover and embrace such modifications within the limits only of the true spirit and scope of the invention.

What is claimed is:

1. A method of reducing oral malodor of a subject comprising placing an effective amount of a yeast of the genus Saccharomyces on the tongue of the subject and allowing the yeast to be activated.

2. The method of claim 1, wherein said yeast is placed on the dorsal portion of the subject's tongue.

3. The method of claim 1, wherein said yeast is placed just before the subject goes to sleep.

4. The method of claim 2, wherein said yeast is placed just before the subject goes to sleep.

5. The method of claim 1 wherein a pill comprising 30 to 100 milligrams of powdered yeast bound by a carrier is dissolved on the tongue of the subject.

6. The method of claim 2 wherein a pill comprising 30 to 100 milligrams of powdered yeast bound by a carrier is dissolved on the tongue of the subject.

7. The method of claim 1 wherein a cream comprising 30 to 100 milligrams of powdered yeast bound by a carrier is dissolved on the tongue of the subject.

8. The method of claim 2 wherein a cream comprising 30 to 100 milligrams of powdered yeast bound by a carrier is dissolved on the tongue of the subject.

9. A method of reducing oral malodor of a subject comprising gargling and rinsing with a solution of powdered yeast of the genus Saccharomyces and water, wherein said solution has a concentration of yeast effective to leave the equivalent of about 30 to 100 milligrams of powdered yeast in the mouth of the subject upon said rinsing and refraining from eating or drinking for a period of time thereafter.

* * * * *